US00PP13154P2

(12) United States Plant Patent
Griesbach et al.

(10) Patent No.: US PP13,154 P2
(45) Date of Patent: Oct. 29, 2002

(54) ORNITHOGALUM PLANT NAMED 'CHESAPEAKE SUNSET'

(75) Inventors: Robert Griesbach, Ellicott City, MD (US); Fred Meyer, deceased, late of Escondido, CA (US), by Marlene Estella Meyer, administrator

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/765,317

(22) Filed: Jan. 22, 2001

(65) Prior Publication Data

US 2002/0100089 P1 Jul. 25, 2002

(51) Int. Cl.[7] ..... A01H 5/00
(52) U.S. Cl. ..... Plt./263

(58) Field of Search ..... Plt./263

(56) References Cited

PUBLICATIONS

U.S. National Arboretum Plant Introduction, Floral and Nursery Plants Research Unit, Ornithogalum 'Chesapeake Blaze', 'Chesapeake Sunburst', and 'Chesapeake Sunset', Nov. 1999.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ornithogalum plant named 'Chesapeake Sunset' characterized by its strong, upright, and short scapes; dense corymbose racemes with numerous orange-colored flowers; and glossy dark green leaves.

2 Drawing Sheets

BACKGROUND OF THE INVENTION

The present Invention relates to a new and distinct cultivar of Ornithogalum plant, botanically known as *Ornithogalum hybrida*, and hereinafter referred to by the name 'Chesapeake Sunset'.

The new Ornithogalum is a product of a planned breeding program conducted by the Inventors in Beltsville, Md. and Escondido, Calif. The objective of the breeding program was to create new freely-flowering interspecific Ornithogalum hybrids with unique and desirable flower colors.

The new Ornithogalum originated from a cross made by the Inventors of a proprietary selection of *Ornithogalum dubium* identified as 270-4, not patented, as the male, or pollen, parent with the *Ornithogalum hybrida* cultivar Sunshine (*Ornithogalum dubium*×*O. multifolium*), not patented, as the female, or seed, parent. The cultivar Chesapeake Sunset was discovered and selected by the Inventors as a flowering plant within the progeny of the stated cross in a controlled environment in Beltsville, Md. in 1993.

Asexual reproduction of the new Ornithogalum by tissue culture in a controlled environment in a laboratory in Beltsville, Md., has shown that the unique features of this new Ornithogalum are stable and reproduced true to type in successive generations.

SUMMARY OF THE INVENTION

The cultivar 'Chesapeake Sunset' has not been observed under all possible environmental conditions. The phenotype may vary somewhat with variations in environment such as temperature, daylength, light intensity, and water or nutritional status without, however, any variance in genotype.

The following traits have been repeatedly observed and are determined to be the unique characteristics of 'Chesapeake Sunset'. These characteristics in combination distinguish 'Chesapeake Sunset' as a new and distinct Ornithogalum:

1. Strong, upright and short scapes.
2. Dense corymbose racemes with numerous orange-colored flowers.
3. Glossy dark green leaves.

In side-by-side comparisons conducted by the Inventors in Beltsville, Md., plants of the new Ornithogalum differ from plants of the female parent, the cultivar Sunshine, in the following characteristics:

1. Plants of the new Ornithogalum have longer leaves than plants of the cultivar Sunshine.
2. Plants of the new Ornithogalum have stronger scapes than plants of the cultivar Sunshine.
3. Plants of the new Ornithogalum have orange-colored flowers whereas plants of the cultivar Sunshine have yellow-colored flowers.

In side-by-side comparisons conducted by the Inventors in Beltsville, Md., plants of the new Ornithogalum differ from plants of the male parent, the selection 270-4, in the following characteristics:

1. Plants of the new Ornithogalum are more freely flowering than plants of the selection 270-4.
2. Plants of the new Ornithogalum have stronger scapes than plants of the selection 270-4.
3. Plants of the new Ornithogalum have larger flowers than plants of the selection 270-4.

DESCRIPTION OF THE PHOTOGRAPHS

The accompanying colored photographs illustrate the overall appearance of the new Ornithogalum, showing the colors as true as it is reasonably possible to obtain in colored reproductions of this type. Colors in the photographs may differ slightly from the color values cited in the detailed botanical description which accurately describe the colors of the new Ornithogalum.

The photograph on the first sheet comprises a close-up view of a typical inflorescence of 'Chesapeake Sunset'.

The photograph on the second sheet comprises a close-up view of a typical flowering inflorescence of 'Chesapeake Sunset'.

DETAILED BOTANICAL DESCRIPTION

In the following description, color references are made to The Royal Horticultural Society Colour Chart except where general terms of ordinary dictionary significance are used. The following observaitons and measurements describe plants grown in Beltsville, Md., under commercial practice in a glass-covered greenhouse. During the production of the plants, day temperatures ranged from 18 to 27° C. and night temperatures ranged from 13 to 21° C. Measurements and numerical values represent averages for typical flowering plants. Plants used for the description and photograph were grown in 12.5-cm containers for about 20 to 25 weeks after planting rooted tissue-cultured plantlets in the fall.

Botanical classification: *Ornithogalum hybrida* cultivar Chesapeake Sunset.

Parentage:

*Male parent*.—Proprietary selection of *Ornithogalum dubium* identified as 270-4, not patented.

*Female parent.—Ornithogalum hybrida* cultivar Sunshine (*Ornithogalum dubium*×*O. multifolium*), not patented.

Propagation:

*Type*.—Tissue culture.

*Time to initiate roots from tissue-cultured micro-cuttings*.—About 10 days at 24° C.

*Root description*.—Quantity: About 20 to 30 primary roots arising from bulb. Diameter: About 7 to 9 cm. Color: 159C.

*Bulb description*.—Appearance: Tunicate. Diameter: About 3 cm. Circumference: About 8 to 9 cm. Color: 161B.

Plant description:

*Plant form*.—Upright flowering potted plant; inverted triangle. Leaves basal with central flowering stem. Flowers arranged in dense corymbose racemes.

*Crop time*.—Usually about 20 to 25 weeks are required to produce finished flowering plants in 12.5-cm containers from rooted tissue-culture plantlets.

*Plant height*.—About 7 to 10 cm.

*Plant width*.—About 16 to 18 cm.

*Leaves*.—Arrangement: Simple; basal; rosette; sessile. Quantity of leaves per plant: About 4 to 8. Length: About 7 to 8 cm. Width: About 3 cm. Shape: Linear. Apex: Acute. Margin: Entire. Texture, upper and lower surfaces: Glabrous, smooth. Color: Young leaves, upper and lower surfaces: 144A. Mature leaves, upper and lower surfaces: 137A, upper surface, glossy; venation, 137A. Leaf sheath: Length: About 1.5 cm. Width: About 1.8 cm. Color: 155B.

Flower description:

*Flowering habit*.—Inflorescences scapose with single flowers, 3-merous, arranged in dense corymbose racemes. Flowers not fragment; flowers persistent.

*Natural flowering season*.—Plants flower during the spring.

*Flower longevity on the plant*.—About one month.

*Flower longevity as a cut flower*.—About 3 to 4 weeks.

*Inflorescence size*.—Length: About 7 cm. Width: About 4 cm.

*Flower buds*.—Length: About 1.2 to 1.5 cm. Diameter: About 8 to 10 mm. Shape: Ovoid. Color: 137A.

*Flowers*.—Quantity of flowers and flower buds per plant: About 20 to 25 per flowering stem; each bulb produces about 1 to 3 flowering stems. Shape: Circular. Diameter: About 3 cm. Depth (height): About 1.5 cm.

*Perianth*.—Quantity/arrangement: Three petals and three sepals per flower; imbricate; separate. Lengh: About 1.5 cm. Width: About 1 cm. Shape: Pyriform. Apex: Slightly acute. Margin: Entire. Texture, upper and lower surfaces: Smooth, waxy. Color: When opening, upper and lower surfaces: 25A. Fully opened, upper and lower surfaces: Apex and center, 25A; base, 152A; glossy.

*Scape*.—Angle: Erect. Strength: Strong. Length: About 5 cm. Diameter: About 1 cm. Texture: Glabrous. Color: 137A.

*Pedicels*.—Strength: Strong. Length: About 3 to 3.5 cm. Diameter: About 3 mm. Texture: Glabrous. Color: 137A.

*Flower bracts*.—Arrangement: Single, subtending the perianth. Length: About 2.5 cm. Width: About 1 cm. Shape: Cymbiformis. Color: 137A.

*Reproductive organs*.—Stamens: Quantity: Six. Anther shape: Oval. Anther length: About 3 to 5 mm. Anther color: 14B. Amount of pollen: Abundant. Pollen color: 14B. Pistils: Quantity: One. Lenght: About 6 to 8 mm. Stigma shape: Tri-sulcate. Stigma color: 166C. Style length: About 3 to 4 mm. Style color: 166C. Ovary color: 147A.

*Seed*.—Seed production has not been observed.

Disease resistance: Resistance to pathogens common to Ornithogalums has not been determined.

It is claimed:

1. A new and distinct cultivar of Ornithogalum plant named 'Chesapeake Sunset', as illustrated and described.

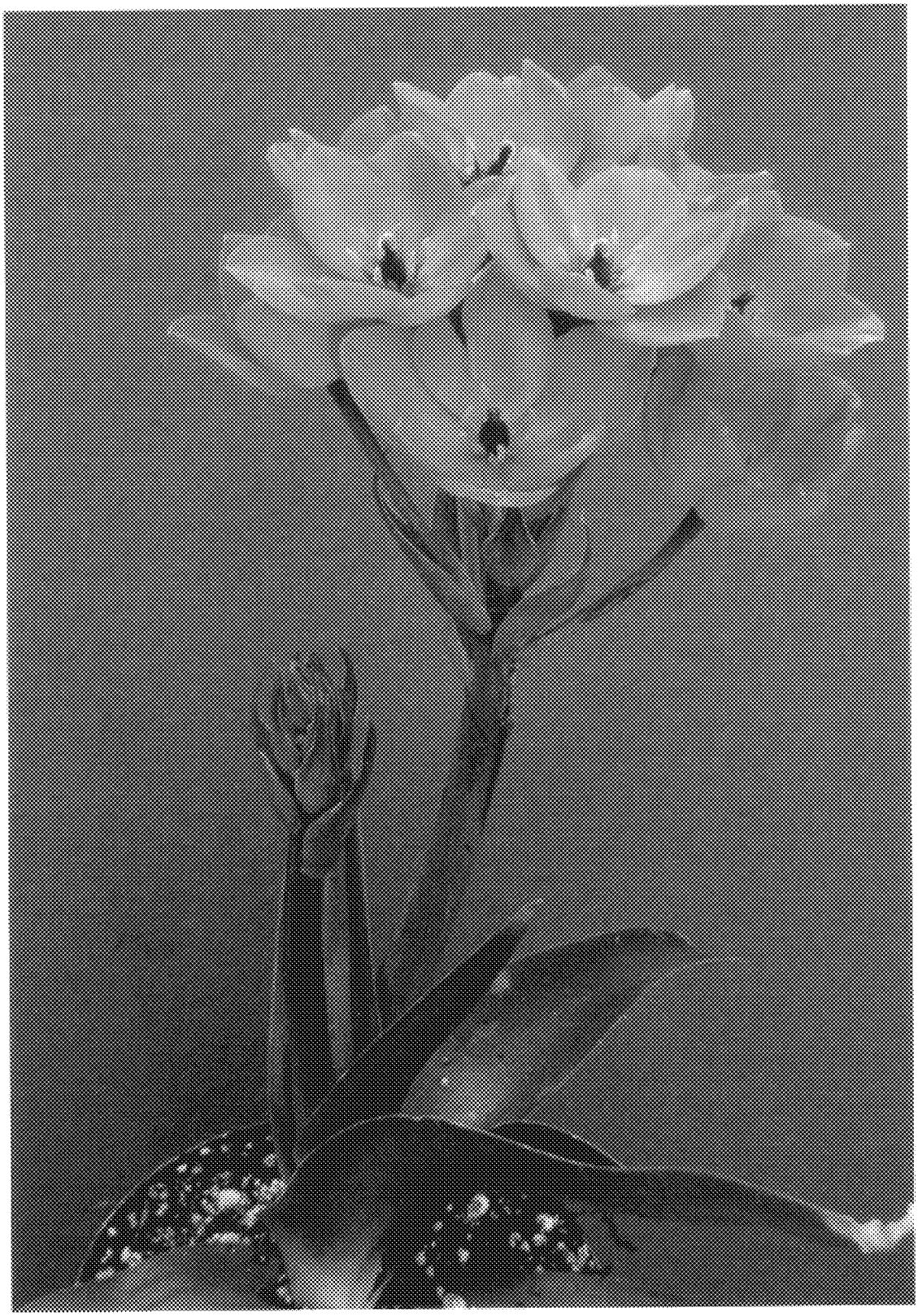

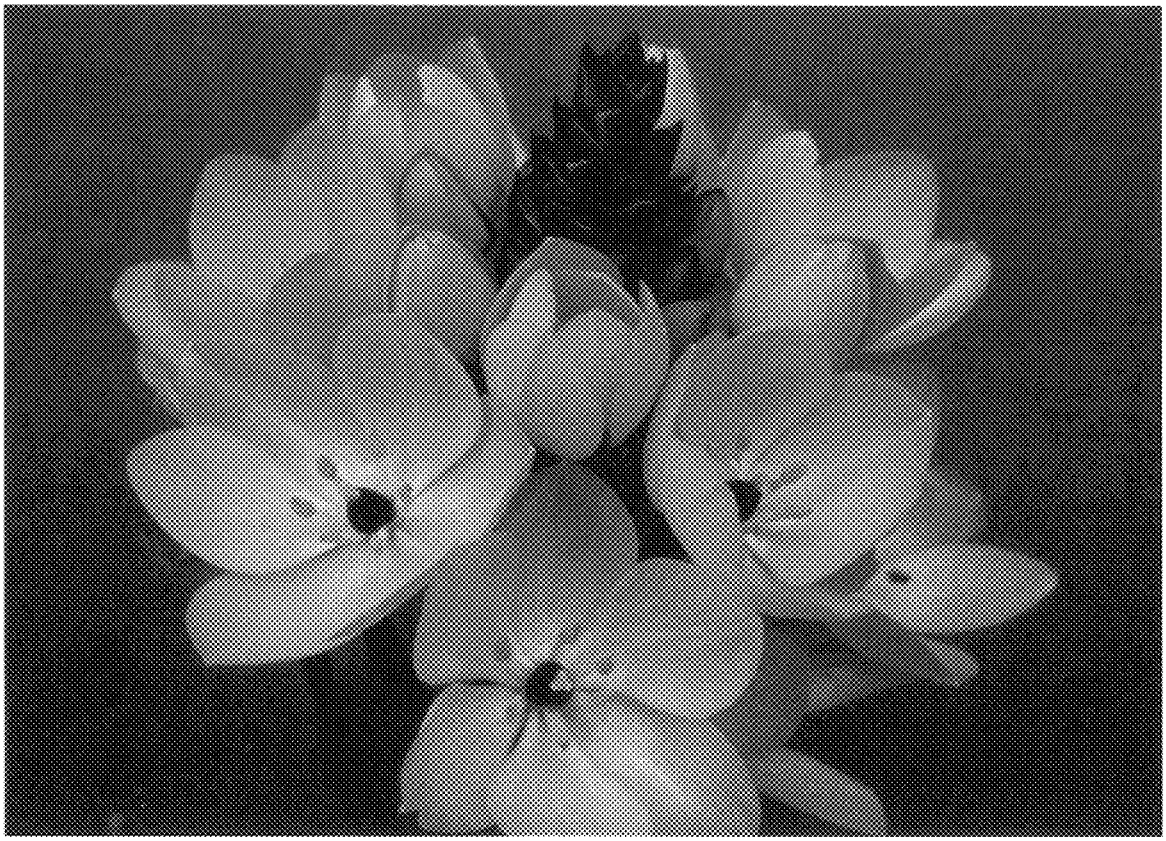

* * * * *